United States Patent [19]

Ishida et al.

[11] 4,279,892

[45] Jul. 21, 1981

[54] ORGANOGERMANIUM INDUCTION OF INTERFERON PRODUCTION

[75] Inventors: Nakao Ishida, Sendai; Hiroshi Satoh, Tokyo; Fujio Suzuki, Sendai; Kouhei Miyao, Tokyo, all of Japan

[73] Assignee: Asai Germanium Research Institute, Tokyo, Japan

[21] Appl. No.: 129,997

[22] Filed: Mar. 13, 1980

[30] Foreign Application Priority Data

Mar. 15, 1979 [JP] Japan ................................. 54/30297

[51] Int. Cl.$^3$ ...................... A61K 45/02; A61K 39/00
[52] U.S. Cl. ......................................... 424/85; 435/811
[58] Field of Search ...................... 424/85; 260/112 R; 435/68, 811

[56] References Cited

U.S. PATENT DOCUMENTS

| 3,719,754 | 3/1973 | Day et al. | 424/85 |
| 3,970,749 | 7/1976 | Baugh | 424/85 |
| 4,130,641 | 12/1978 | Ts'o et al. | 424/85 |

Primary Examiner—Delbert R. Phillips
Assistant Examiner—Blondel Hazel
Attorney, Agent, or Firm—Burns, Doane, Swecker & Mathis

[57] ABSTRACT

Therapeutic induction of interferon production in living animal cells is effected by subjecting such cells to the species-specific interferon inducing effect of an organogermanium compound having the formula:

$$(GeCH_2CH_2COX)_2O_3$$

wherein X is —OH, —NH$_2$ or —O—alkyl.

4 Claims, 5 Drawing Figures

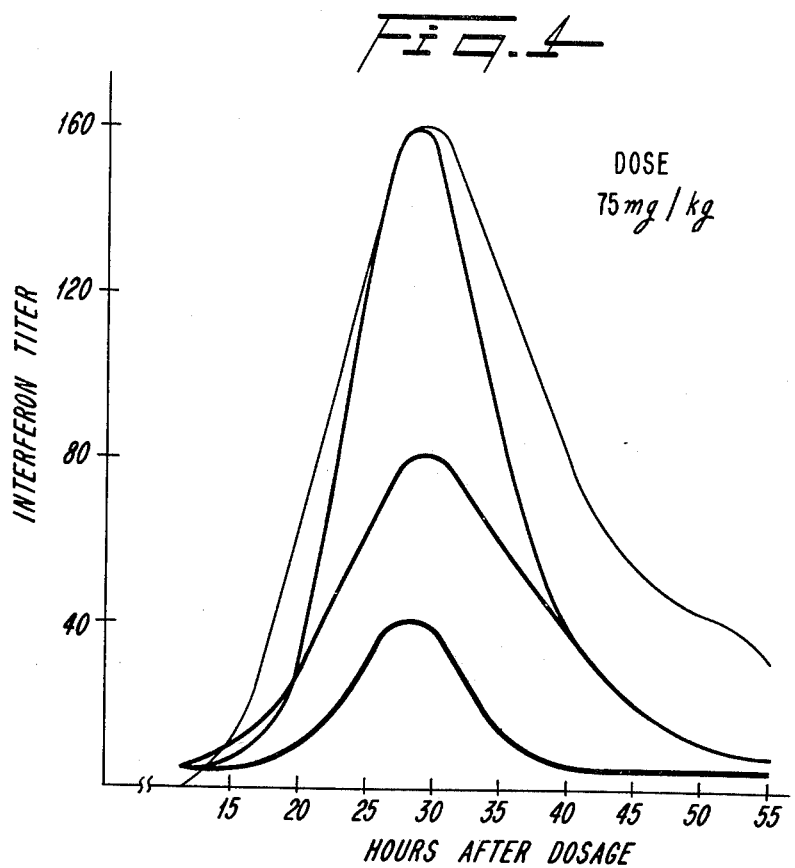
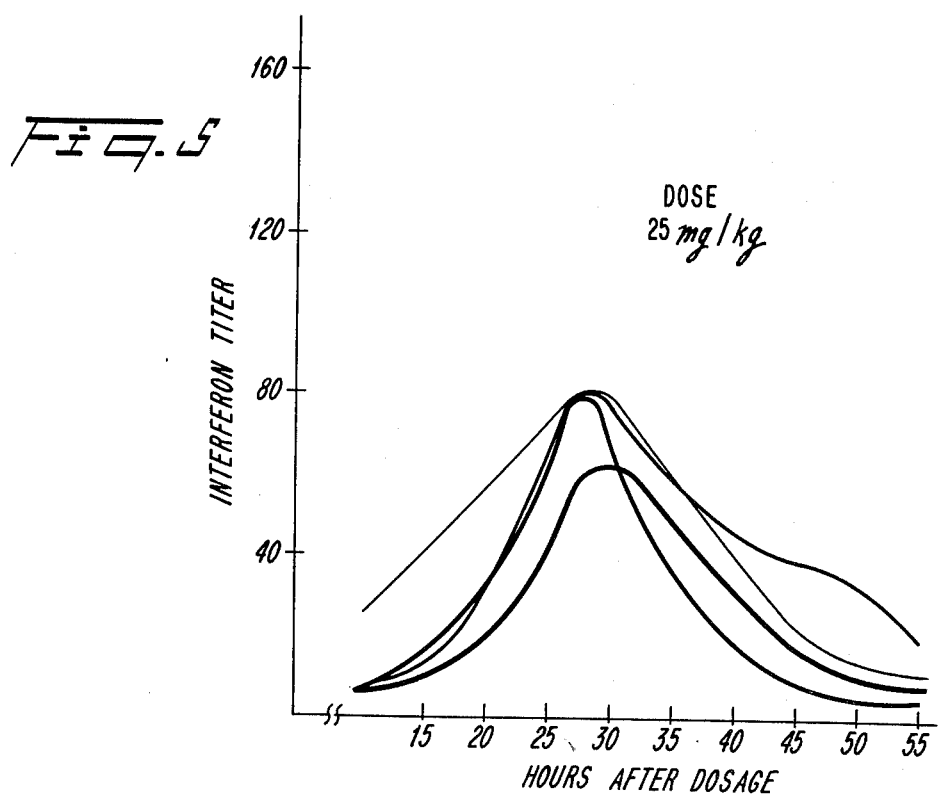

ORGANOGERMANIUM INDUCTION OF INTERFERON PRODUCTION

BACKGROUND OF THE INVENTION

1. Field of the Invention

The present invention relates to induction of interferon production, and, more especially, to the induction of interferon production utilizing certain organogermanium compounds.

2. Description of the Prior Art

Interferon is a known antiviral glycoprotein which is produced in living animal cells in response to the presence of virus, nucleic acid, and even such other substances as polyanionic copolymers. The production of interferon is currently thought to be a normal mechanism of resistance to virus infection possessed by all vertebrate animals and certain insects. It is a factor which exerts its activity when present in but minute amounts. Each interferon is a glycoprotein having a molecular weight of 20,000 to 160,000 and is species specific. Its physiological properties include macrophage migration inhibition, immunity adjustment, and anti-tumor activity, in addition to antiviral activity.

For purposes of inducing interferon production, various substances are known, e.g., nucleic acid, bacterial cells endotoxins, polycarboxylates, polyphosphates, polysaccharidesulfates and phosphorylated dextrans, and same have been deemed "interferon inducers". Typically, such inducers are macromolecular compounds, and most are highly toxic, are antigenic or display pronounced allergic toxicity. Therefore, such inducers are of little value as clinical medicines. Several non-macromolecular interferon inducing agents too are known, such as CP-20961 and tilorone hydrochloride but these are also characterized by one or more adverse side effects.

SUMMARY OF THE INVENTION

Accordingly, a major object of the present invention is the provision of a novel class of interferon inducers, but which class is conspicuously devoid of those aforementioned drawbacks and disadvantages which to date have characterized this art.

Briefly, the present invention features the induction of interferon production with certain organogermanium compounds having the formula I:

$$(GeCH_2CH_2COX)_2O_3 \qquad [I]$$

wherein X is selected from the group consisting of —OH, —NH$_2$ and —O—alkyl, preferably lower alkyl, and which organogermanium compounds are both low in molecular weight and are strikingly low in toxicity.

BRIEF DESCRIPTION OF THE DRAWINGS

FIGS. 4 and 5 are graphs illustrating the amount, or titer, of interferon induced upon administration of the organogermanium compounds of the invention to humans, versus time lapse.

DETAILED DESCRIPTION OF THE INVENTION

Figure 1:
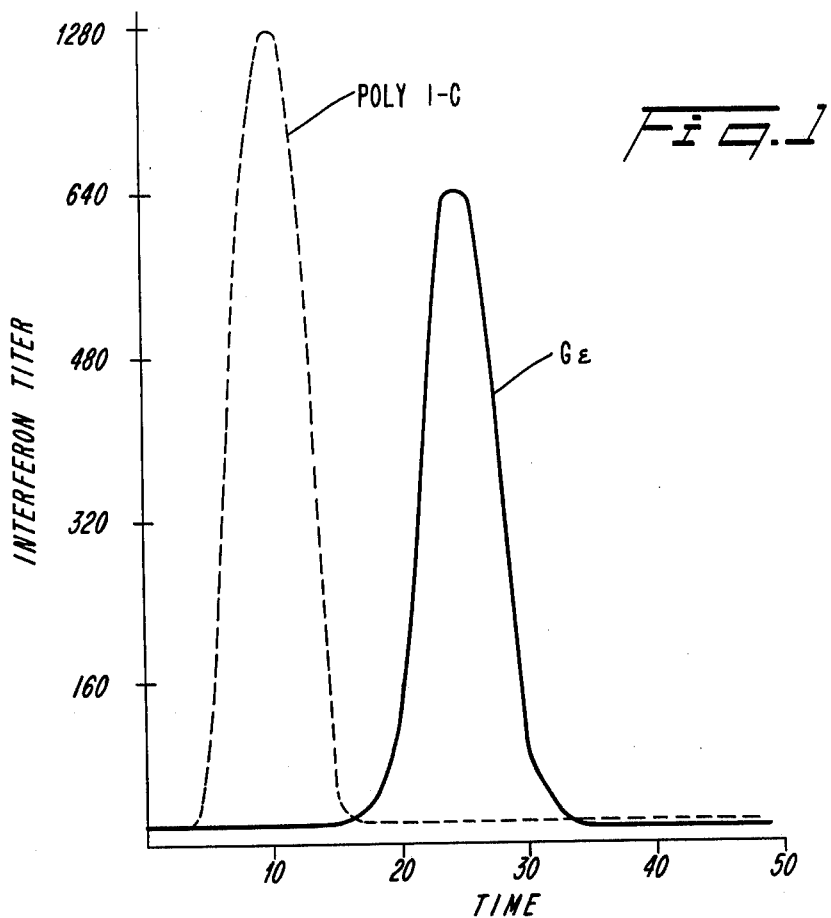
FIG. 1 is a graph reflecting the amount, or titer, of interferon induced versus time lapse, upon administration of the organogermanium compounds of the invention to DDI mice.

More particularly, those organogermanium having the above formula [I] are conveniently prepared by any one of a number of facile methods. For example, a compound of the formula [I] in which X is an —OH group, i.e., carboxyethyl germanium sesquioxide, is conveniently prepared by hydrolyzing cyanoethyltrichlorogermane with hydrochloric acid or sulfuric acid, or by reacting trichlorogermane with acrylic acid to form trichlorogermanopropionic acid and hydrolyzing the thus formed trichlorogermanopropionic acid, or by chlorinating trichlorogermanopropionic acid to form trichlorogermanopropionyl chloride and hydrolyzing the thus obtained trichlorogermanopropionyl chloride.

Furthermore, the compounds represented by the above formula [I] can also be conveniently prepared by reacting a trihalogermane having the following formula:

$$X_3GeH \qquad [II]$$

wherein X is a halogen atom, with chloropropionic acid or derivative thereof having the following formula:

$$ClCH_2CH_2COR \qquad [III]$$

wherein R represents an —OH, —NH$_2$ or —O—alkylene group, preferably lower alkylene to form a compound having the following formula:

$$X_3GeCH_2CH_2COR \qquad [IV]$$

wherein X and R are as defined above, and hydrolyzing the thus formed compound of the formula [IV].

One of the characteristic features of the interferon inducing agent of the present invention is that its toxicity is extremely low. For example, in the case of carboxyethyl germanium sesquioxide, its LD$_{50}$ value is in excess of 6300 mg/kg of body weight of mice and is greater than 10 g/kg of body weight of rats upon oral administration. Upon intravenous injection, the LD$_{50}$ value is larger than any physically practicable maximum amount, i.e., 1000 mg/kg of body weight, for either mice or rats. Furthermore, during a chronic toxicity test, no rat died from any of the test groups to which the interferon inducing agent of the invention was orally administered over a period of six months in a dosage amount of 30 mg, 300 mg or 3000 mg per kg of body weight per day, and no pathological disorder was observed. In the case where the interferon inducing agent was intravenously injected into dogs over a period of six months in a dosage amount of 500 mg per kg of body weight per day, no toxicity was found. Such extremely low toxicity is indeed rare upon administration of the "conventional" interferon inducing agents.

The interferon induced by the organogermanium compounds of the present invention has been proved to be Type II interferon, or the so-called "immune interferon", and it was also confirmed that such interferon was a factor in activating macrophage and that any macrophage thus activated displayed marked cytotoxicity, i.e., cell-kill activity against such foreign cells as cancer cells. Thus, the organogermanium compounds according to the present invention can be said to be immuno modulators, as well as inducers of interferon production, and same, additionally, are useful chemotherapeutics.

In order to further illustrate the present invention and the advantages thereof, the following specific examples are given, it being understood that same are intended only as illustrative and in nowise limitative. In said examples to follow, the novel interferon inducer according to the invention is designated simply as "Ge".

EXAMPLE 1

In this example, the antiviral activity, or ability to inhibit viral replication, of the interferon inducer, Ge, is demonstrated.

A 300 mg/kg dose of Ge was orally administered to each of a group of 30 DDI six-week-old mice as the test group. As the positive control group, 30 mice were treated intraperitoneally with a 0.5 mg/kg dose of a double-stranded complex polyriboinosinic acid and polyribocytidylic acid (Poly 1-C). In addition, saline solution was administered to another 30 mice, as a placebo control group. From each group, blood samples were taken from five mice at intervals of 1, 5, 10, 15, 20, 25, 30 and 50 hours after administration. The blood was subjected to centrifugation at 3,000 rpm for 15 minutes to separate the serum. Quantitative analysis of the viral infection inhibitory agent induced in the mouse sera was carried out in the following manner: Three-day-old L-1D cells, cultured in small tubes with Eagle's MEM supplemented 10% bovine serum (culture medium), were pretreated with the sera for 18–24 hours. Then cells were washed twice with the maintenance medium (Eagle's MEM+2% bovine serum). Same were then infected with vesicular stomatitis virus (VSV) at 100 $TCD_{50}$ (50% tissue culture infected dose)/ml. After 18–24 hours cultivation at 37° C., same were microscopically examined in order to determine the inhibitory activity against viral infection.

The antiviral titer is expressed as the reciprocal of the greatest dilution of the serum which significantly inhibits the viral cytopathic effect (CPE). As shown in FIG. 1, viral infection inhibitory activity was detected in the serum of the mice 25 hours after Ge administration.

EXAMPLE 2

To determine the dose dependency of the Ge on the induction of viral infection inhibitory activity, this test was carried out in the same manner as described in Example 1, except that the dosages of the Ge were varied.

Figure 2:
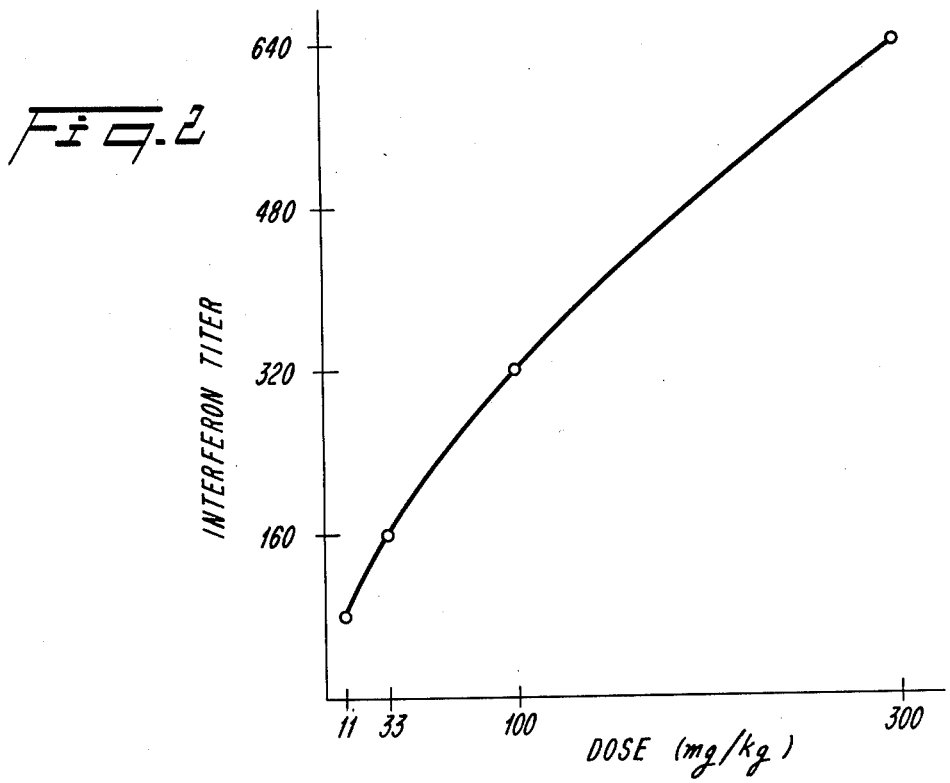
FIG. 2 is a graph illustrating the relationship between the amount, or titer, of interferon induced and the dosage amount administered of the organogermanium compounds according to the invention.

The results obtained are as shown in FIG. 2. The peak titer of viral infection inhibitory activity was determined to be 25 hours upon Ge administration. From said FIG. 2, it will be seen that the ability of the Ge to induce the antiviral response, or to display significant viral infection inhibitory activity, is dose dependent and that, the higher the dosage amount, the greater the titer of the antiviral agent in circulation.

EXAMPLE 3

In order to examine certain biological properties of the viral infection inhibitory activity induced by the agent Ge, the following experiment was conducted: Twenty mice, each weighing 20-22 g, and three human volunteers, were each given Ge orally in dosage amounts of 300 (mouse) and 75 (human) mg/kg. Twenty-five hours (mouse) or thirty hours (human) after administration, blood samples were taken and subjected to centrifugal separation for 15 minutes at 3,000 rpm. Two types of serum were thus prepared. As to each serum, the viral infection inhibitory effect was investigated using the primary culture cells of human embryonic lung and L-1D cells in the same manner as described in Example 1.

The results are shown in Table 1. As reported in said Table 1, the viral infection inhibitory or antiviral agent induced upon administration of the Ge in mice displayed resistance to viral infection only in the L-1D cells and no inhibitory activity as regards viral infection in primary cultures of human embryonic lung and chicken embryonic cells was shown. Similarly, the viral infection inhibitory or antiviral agent induced upon administration of the Ge in human volunteers displayed antiviral activity only in human cells. Accordingly, it can be concluded that the viral infection inhibitory factor induced upon administration of the Ge is indeed species specific.

TABLE 1

| Interferon Group | Interferon Titer/1 ml serum | | |
|---|---|---|---|
| | L-1D cell | Human embryonic lung cell | Chicken embryonic cell |
| Mouse | 640 | <20 | <20 |
| Human | <20 | 160 | <20 |

EXAMPLE 4

In order to examine certain physico/chemical properties of the viral infection inhibitory factor induced in the mouse serum by administration of the Ge in accordance with that method outlined in Example 1 and that induced in mouse serum by administration of Poly 1-C to the positive control group, the following experiments were conducted: One series was heated for one hour at 56° C. Another series was adjusted to pH 2.0 by dialyzing against a pH 2.0 buffer (1/100 M glycin-HCl buffer) and maintained for 18 hours at 4° C. Next, the series was again adjusted to pH 7.2, by redialyzing against 1/100 M PBS. Yet another series was treated with trypsin having a 1000 mcg/ml final concentration, at 37° C. for 3 hours. In the above test, viral infection inhibitory activity was determined in accordance with the procedure set forth in Example 1.

The results are reported in Table 2. As there summarized, the viral infection inhibitory factor induced in the mouse serum upon administration of Ge was unstable to thermal treatment at 56° C. for one hour and also to acidification to pH 2.0; and its protein was trypsin labile. The properties of such factor are not similar to those of the interferon induced upon administration of Poly 1-C, excluded the trypsin lability.

As concluded herefrom and from Examples 1 and 3, the viral infection inhibitory or antiviral agent induced in mouse serum upon administration of Ge was determined to be interferon. Particularly from the results of the thermal and acid treatments, such antiviral agent induced in mouse serum by the Ge was concluded to be an immune (type II) interferon

TABLE 2

| Treatment | Ge (Remaining amount of titer, %) | Poly I-C (Remaining amount of titer, %) |
|---|---|---|
| 56° C., heating 1 hr. | 20 (<3.1) | 640 (100) |
| pH 2.0, 4° C., standing for 18 hrs. | 20 (<3.1) | 640 (100) |
| Trypsin-treatment (1000 mcg/ml), 37° C., 3 hrs. | 20 (<3.1) | 20 (<3.1) |
| Untreated (kept in refrigerator) | 640 (100) | 640 (100) |

EXAMPLE 5

It is known that interferon has the ability to convert a standing macrophage into a tumoricidal macrophage, deemed activated macrophage (A-MΦ), either in vivo or in vitro. Since the Ge induced the formation of immune interferon in vivo, it was expected that A-Mφ would be induced in the Ge treated animal.

Accordingly, the following tests were carried out and the results reported in Table 3 were obtained. Peritoneal exudate cells obtained from mice 72 hours after treatment with a 300 mg/kg dose of Ge were cultured for 20 minutes in a petri dish utilizing RPMI-1640 medium supplemented with 10% fetal calf serum. Cells adhering to the petri dish, obtained by washing with the same culture medium, were separately co-cultured with FM-3A cells as the target tumor cells, in a ratio of 10:1. FM-3A cells were cultured singly, or with macrophages derived from normal mice, as the control. In each run, the growth of FM-3A cells was monitored. A determination of the number of FM-3A cells was carried out per the dye exclusion test using Trypan-Blue. As will be seen from the results reported in Table 3, the growth of FM-3A cells 48 hours after cultivation was prominently inhibited only in the event of the co-culturing with the macrophages obtained from the Ge treated mice. Thus, it is apparent that Ge induces the formation of A-MΦ in live mice.

TABLE 3

| Culture system | Cell number after 48 hours cultivation | Growth inhibitory rats (%) |
|---|---|---|
| FM-3A alone | 4.8 × 10$^5$ | 0 |
| FM-3A MΦ derived from normal mice | 4.4 × 10$^5$ | 8 |
| FM-3A MΦ derived from Ge treated mice | 2.5 × 10$^5$ | 48 |

EXAMPLE 6

Ge was administered orally in a dose of 300 mg/kg to 50 male DDI mice (six-weeks-old). Twenty-five hours later, the mice were sacrificed and serums collected as Ge induced interferon samples in mice. Eighteen ml of serum were obtained.

The anti-tumor activity of the aforementioned sera, constituting the Ge-induced interferon specimens, was examined in tumor bearing mice. Serum collected from mice treated with physiological saline was used as a control. 4×10$^3$ cells/mouse of MEP-II tumor cells which were induced by 3-methylcholanthrene in DDI mice were inoculated into the peritoneal cavity of 40 mice.

Ten mice out of the 40 were given the serum interferon derived from the Ge-treated mice. Another group of ten mice was given the serum obtained from the saline treated mice, and the remainder were treated with physiological saline. Administration of sera was commenced 24 hours after transplantation and was conducted once daily for 5 days, at a dose of 0.2 ml per day.

As will be seen from the results reported in Table 4, a significant number of survivors came only from the Ge-induced interferon-administered group. Thus, it too will be seen that Ge-induced interferon displays marked anti-tumor activity.

TABLE 4

| Treatment | Number of mice treated | Days surviving | Survival rate (%) |
|---|---|---|---|
| Serum IF derived from Ge-treated mouse | 10 | >95.5 | 6/10 (60) |
| Serum derived from normal mouse | 10 | 28.0 | 0/10 (0) |
| Physiological saline | 20 | 27.2 | 0/20 (0) |

EXAMPLE 7

An anti-tumor activity test of peritoneal exudate cells obtained from mice treated with Ge in a dosage amount of 300 mg/kg was conducted on Ehrlich ascites tumor bearing mice.

1×10$^4$ cells/mouse of Ehrlich ascites tumor cells were transplanted into the peritoneal cavity of DDI mice. Twenty-four hours later, these mice were intraperitoneally supplied with 5×10$^5$ peritoneal exudate cells obtained from mice treated with Ge once daily for six consecutive days. Peritoneal exudate cells obtained from saline injected mice were likewise supplied to tumor bearing mice as a control.

Figure 3:
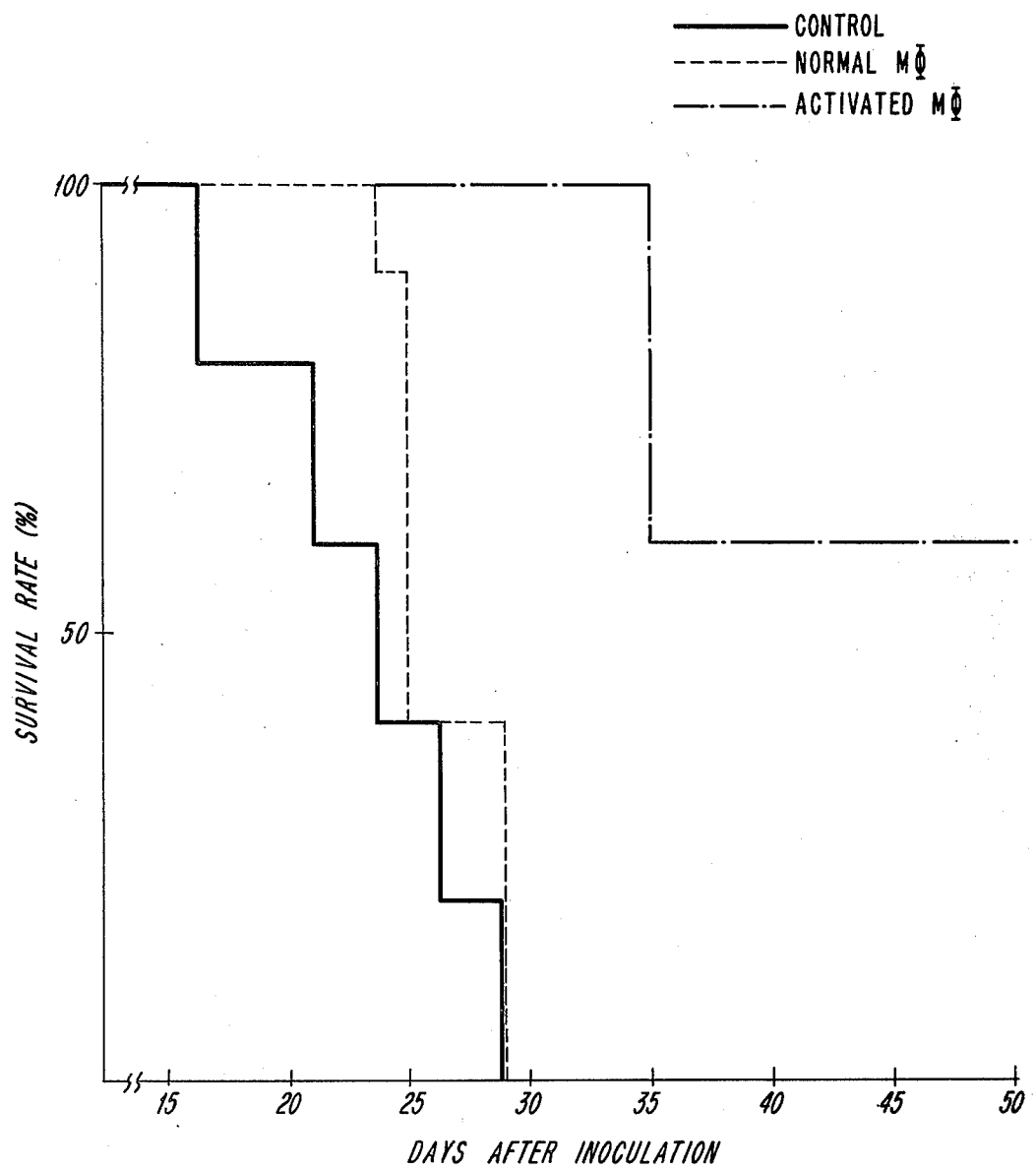
FIG. 3 is a graph illustrating the effect of abdominal cavity macrophage activated by the organogermanium  compounds of the invention on the percentage of survival of Ehrlich ascites tumor bearing mice.

The survival rates of the three groups were compared. As shown in FIG. 3, the macrophage activated by Ge treatment exhibited marked anti-tumor activity.

EXAMPLE 8

4×10$^3$ MEP-II tumor cells were transplanted intraperitoneally in DDI mice as described above. Twenty-four hours later, Ge was orally administered, once daily for seven consecutive days at a daily dosage of 100 or 300 mg/kg to ascertain any anti-tumor effect. In a control group, 0.2 ml of physiological saline solution was orally administered, also once daily for seven days. As will be seen from the results reported in Table 5, both dosage amounts of Ge exhibited anti-tumor activity.

From the foregoing and from the various results of the several experiments, it is apparent that Ge is an effective interferon inducer. The interferon induced facilely converts a standing macrophage into an A-MΦ which either kills or seriously injures tumor cells and, accordingly, the mice thus treated are well adapted for survival.

TABLE 5

| Treatment | Number of mice | Mean survival day | Survival rate (%) |
|---|---|---|---|
| Ge 300 mg/kg | 20 | >102.0 | 55 |
| Ge 100 mg/kg | 20 | >98.8 | 35 |
| Physiological Saline 0.2 ml/mouse | 40 | 29.6 | 0 |

EXAMPLE 9

Capsules of Ge were orally administered to eight healthy volunteers, 21 to 23 years old. The dose administered to one group (two men and two women) was 75 mg/kg and that administrated to the other group (two men and two women) was 25 mg/kg. Serum samples were collected at predetermined intervals, the interferon titers were determined, and the results reflected in FIGS. 4 and 5 were obtained. In the 75 mg/kg-dose group, significant production of interferon was observed in each case. In the 25 mg/kg-dose group, production of interferon was observed, although the level was lower. The reported results thus evidence that Ge induces A-MΦ in humans as well as in mice.

As is apparent from the foregoing results, the interferon inducing agent of the present invention produces an immune interferon which exerts anti-tumor activity by activating macrophage. Furthermore, this interferon inducing agent is extremely low in toxicity when compared to the known interferon inducing agents. Therefore, the interferon inducing agent of the present invention is, additionally, a very valuable carcinostatic agent.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A method for therapeutically inducing interferon production in living animal cells, comprising subjecting said cells to the species-specific interferon inducing effect of an effective amount of an organogermanium compound having the formula:

$$(GeCH_2CH_2COX)_2O_3$$

wherein X is selected from the group consisting of —OH, —NH$_2$ and —O—alkyl.

2. The method as defined by claim 1, wherein X is —OH.

3. The method as defined by claim 1, wherein X is —NH$_2$.

4. The method as defined by claim 1, wherein X is —O—loweralkyl.

* * * * *